United States Patent [19]

Frazier et al.

[11] Patent Number: 5,627,265
[45] Date of Patent: May 6, 1997

[54] RECEPTOR FOR CELL-BINDING DOMAIN OF THROMBOSPONDINS

[75] Inventors: William A. Frazier; Ai-Guo Gao, both of St. Louis, Mo.

[73] Assignee: Washington University, St. Louis, Mo.

[21] Appl. No.: 347,000

[22] Filed: Nov. 30, 1994

Related U.S. Application Data

[63] Continuation-in-part of Ser. No. 29,333, Mar. 5, 1993, Pat. No. 5,399,667.

[51] Int. Cl.⁶ .................. C07K 14/47; C07K 14/705
[52] U.S. Cl. ............................................. 530/350; 530/395
[58] Field of Search ..................... 514/8, 21; 530/350, 530/395

[56] References Cited

U.S. PATENT DOCUMENTS

| | | | |
|---|---|---|---|
| 5,155,038 | 10/1992 | Eyal et al. | 435/240.2 |
| 5,190,918 | 3/1993 | Deutch et al. | 514/15 |
| 5,190,920 | 3/1993 | Baltimore et al. | 514/17 |
| 5,192,744 | 3/1993 | Bouck et al. | 514/8 |
| 5,200,397 | 4/1993 | Deutch et al. | 514/15 |
| 5,256,538 | 10/1993 | Aiken et al. | 436/69 |
| 5,367,059 | 11/1994 | Tuszynski et al. | 530/395 |

FOREIGN PATENT DOCUMENTS

92/17499   10/1992   WIPO ............. C07K 15/00

OTHER PUBLICATIONS

Hay et al, eds., ATCC Catalogue of Cell Lines and Hybridomas, 7th ed., published 1992, pp. 128–130.
Kosfeld & Frazier, J. Biol. Chem. 267, pp. 16230–16236 (1992).
Kosfeld et al., J. Biol. Chem. 266, pp. 24257–24259 (1991).
Dixit et al., Proc. Natl. Acad. Sci. 82, 3472–3476 (1985).
Kosfeld & Frazier, J. Biol. Chem. 268, 8808–8814 (1993).

*Primary Examiner*—Jeffrey E. Russel
*Attorney, Agent, or Firm*—Scott J. Meyer

[57] ABSTRACT

A 52 kDa protein is disclosed, which is a receptor for the cell-binding peptide sequences of the cell-binding domain (CBD) of thrombospondin 1 (TS1), namely the 4N1s and 7N3 peptide sequences as well as the 4N1K and 4NK peptides.

1 Claim, 9 Drawing Sheets

4N1
Arg Phe Tyr Val Val Met Trp Lys Gln Val Thr Gln Ser [SEQ ID NO: 1]
1          5              10

4NK
Lys Arg Phe Tyr Val Val Met Trp Lys Gln Val Thr Gln Ser Lys Lys Tyr
1              5                    10                      15
[SEQ ID NO: 6]

4N1s
Arg Phe Tyr Val Val Met Trp Lys [SEQ ID NO: 2]
1          5

4N1K
Lys Arg Phe Tyr Val Val Met Trp Lys Lys [SEQ ID NO: 7]
1              5                    10

C4
Arg Phe Tyr Val Val Met Trp Lys Gln Val Thr Gln Ser Tyr Trp Asp
1          5              10                      15
Thr Asn Pro Thr Arg Ala Gln Gly Tyr Ser Gly Leu Ser Val
            20              25                  30
[SEQ ID NO: 8]

7N3
Phe Ile Arg Val Val Met Tyr Glu Gly Lys Lys [SEQ ID NO: 4]
1          5              10

C7
Arg Trp Arg Leu Ser His Arg Pro Lys Thr Gly Phe Ile Arg Val Val
1              5                    10                      15
Met Tyr Glu Gly Lys Lys Ile Met Ala Asp Ser Gly Pro Ile
            20              25                  30
[SEQ ID NO: 9]

FIG. 1A

HBD I

Glu Leu Thr Gly Ala Ala Arg Lys Gly Ser Gly Arg Arg Leu Val Lys
1           5                   10                  15
Gly Pro Asp       [SEQ ID NO: 10]

HBD III

Thr Arg Asp Leu Ala Ser Ile Ala Arg Leu Arg Ile Ala Lys Gly Val
1           5                   10                  15
Asn Asp Asn Phe       [SEQ ID NO: 11]
            20

MAL I

Ser Glu Trp Thr Ser Ala Ser Thr Ser Ala Gly Asn Gly Ile Gln Gln
1           5                   10                  15
Arg Gly Arg       [SEQ ID NO: 12]

MAL III

Ser Pro Trp Asp Ile Ala Ser Val Thr Ala Gly Gly Gly Val Gln Lys
1           5                   10                  15
Arg Ser Arg       [SEQ ID NO: 13]

FIG. 1B

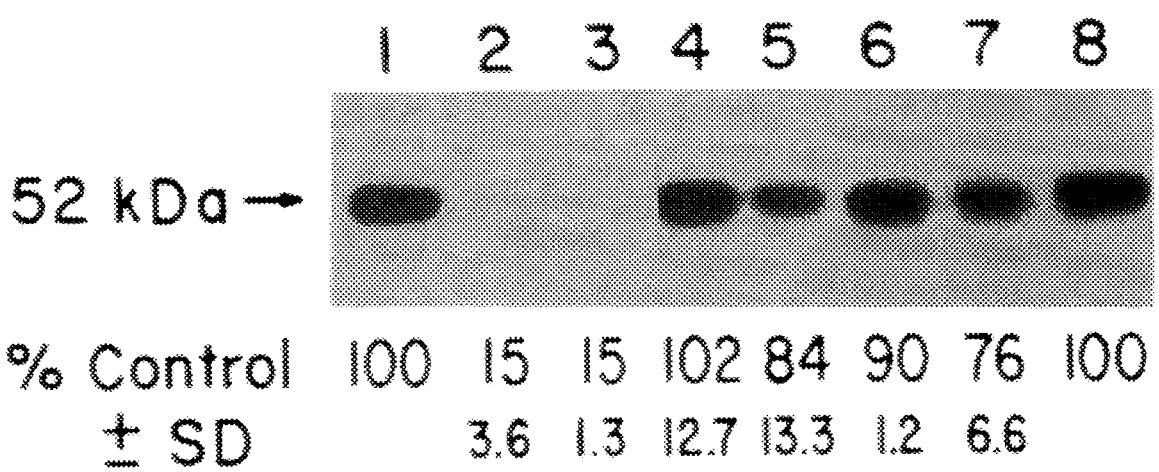
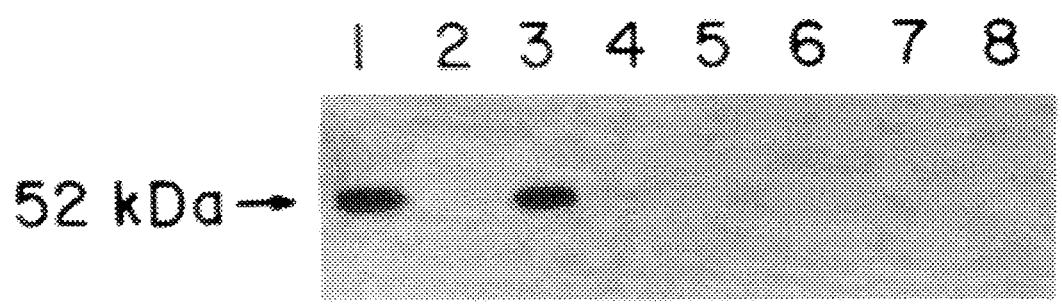

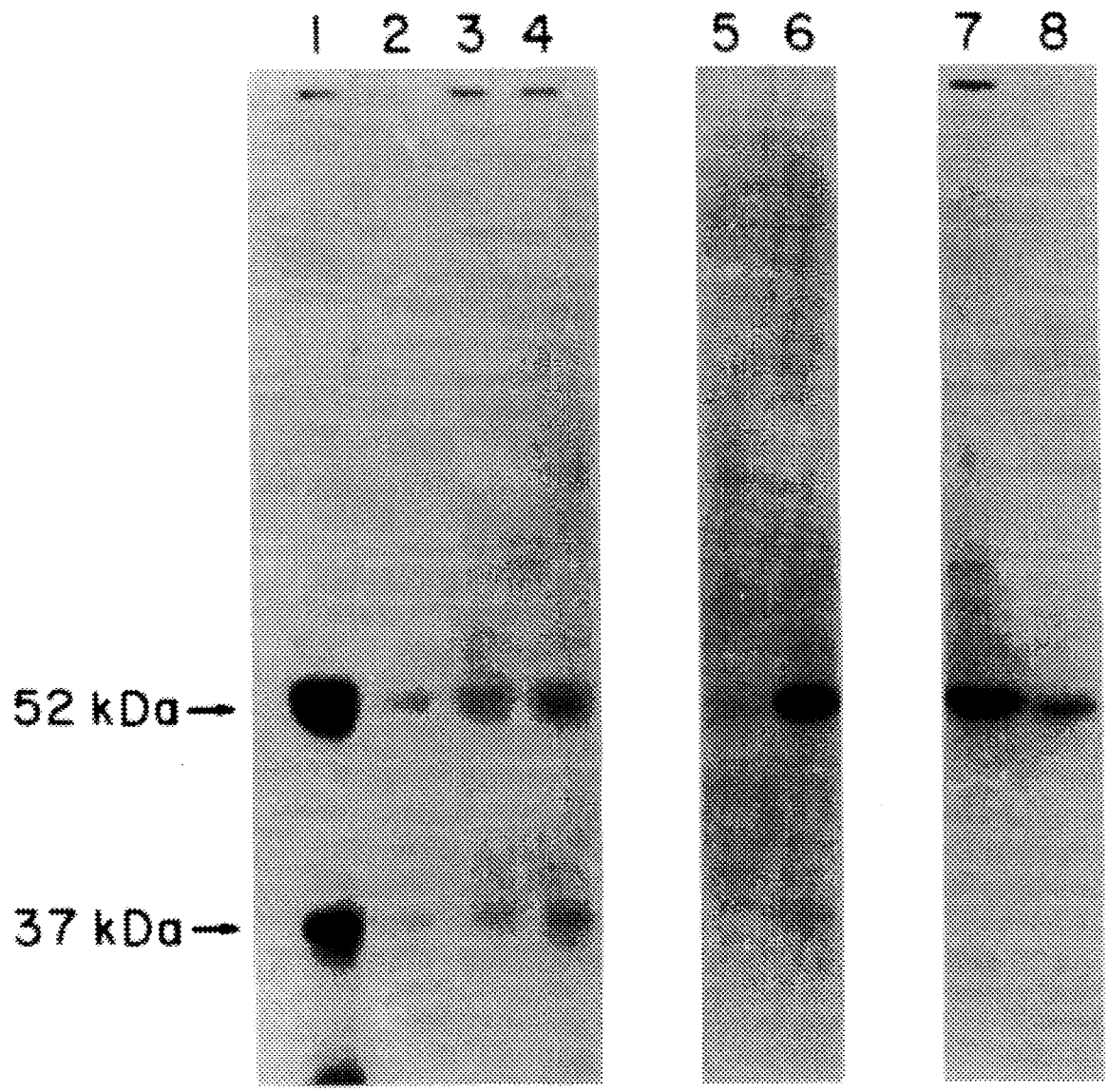

RECEPTOR FOR CELL-BINDING DOMAIN OF THROMBOSPONDINS

CROSS-REFERENCE TO RELATED APPLICATION

This is a Continuation-in-Part of application Ser. No. 08/029,333, filed Mar. 5, 1993, now U.S. Pat. No. 5,399,667, the disclosure of which is incorporated herein by reference.

BACKGROUND OF THE INVENTION

The present invention relates to a receptor for the carboxyl-terminal cell-binding domain (CBD) of thrombospondins and, more particularly, to a novel 52 kDa protein which is a receptor for the cell-binding sequences in the CBD of thrombospondin 1 (TS1).

(Note: Literature references on the following background information, and on conventional test methods and laboratory procedures well known to the ordinary person skilled in the art, and other such state-of-the-art techniques as used herein are indicated in parentheses, and appended at the end of the application).

The thrombospondins (TS) are a family of multidomain glycoproteins (1) that influence the migration, attachment, proliferation and differentiation of a number of cell types.

The highly regulated expression of the TS isoforms during development indicates that they have important roles in developmental processes (2).

In addition, TS plays an important role in processes like wound healing (3,4), tumorigenesis (5), and angiogenesis (6–8).

The effects of TS1 and other isoforms on cells are mediated through the interaction of several domains within the complex TS structure with a number of cell surface receptors. For example, the heparin-binding domain (HBD) of TS1 binds to cell surface heparin (heparan) sulfate proteoglycans (HSPGs) (9), chondroitin sulfate proteoglycans (10), and sulfatides (11) on many different cell types.

The single RGD sequence within the type 3 or calcium-binding repeats of TS1 binds to $\alpha_v\beta_3$ integrins on some cells (12), and the Thr-Cys-Gly-containing sequence in the type 1 or properdin (malaria)-like repeats of TS1 and TS2 binds to CD36 on platelets, monocytes, endothelial cells and some tumor cells (13–15).

In addition to these sites in TS1, the carboxyl-terminal domain has been identified as a binding site for many types of normal and transformed cells (16). This domain is adjacent in the linear amino acid sequence of TS1 to the RGD sequence in the last of the type 3 repeats (17). To determine if the RGD sequence was necessary for the cell adhesion activity of the C-terminal domain, this region of TS1 was expressed in *E. coli* from a cDNA construct that began downstream of the RGD sequence (17). The expressed TS1 domain had substantial cell-binding activity even though the RGD sequence was excluded, indicating that this region of TS1 (referred to as the cell-binding domain or CBD) contained one or more novel cell attachment sites (17).

Using overlapping synthetic peptides representing the entire 221 amino acid residues of the CBD, two 30mer peptides with potent attachment activity toward many types of transformed and normal cells were identified (18).

In applicant's application, Ser. No. 08/029,333, filed Mar. 5, 1993, now U.S. Pat. No. 5,399,667, small VVM-containing peptides are disclosed which bind to the TS1 receptor. These peptides preferably have 5–13 amino acid residues which share the tripeptide Val-Val-Met and have the five sequences shown below as SEQ ID NOS: 1–5:

These five peptides were designated for structural purposes as 4N1, 4N1-2, 4N1-1, 7N3 and 7N3-1, respectively.

The two related sequences, 4N1-2 and 7N3-1, were disclosed to be minimal cell-binding sites. Adhesion of cells to either of these peptides is inhibited by the other, suggesting that both interact with the same receptor on cells. See also reference (19).

Various of these VVM-containing peptides, designated by the three-letter abbreviations, are shown in the Sequence Listing herein and in the accompanying Diskette as follows:

| | |
|---|---|
| Arg Phe Tyr Val Val Met Trp Lys Gln Val Thr Gln Ser | [SEQ ID NO: 1] |
| Arg Phe Tyr Val Val Met Trp Lys | [SEQ ID NO: 2] |
| Arg Phe Tyr Val Val Met | [SEQ ID NO: 3] |
| Phe Ile Arg Val Val Met Tyr Glu Gly Lys Lys | [SEQ ID NO: 4] |
| Ile Arg Val Val Met | [SEQ ID NO: 5] |

BRIEF DESCRIPTION OF THE INVENTION

In accordance with the present invention, a novel 52 kDa protein is provided, which is a receptor for the cell-binding sequences in the CBD (cell-binding domain) of thrombospondin 1 (TS1).

The active cell-binding peptides (VVM-containing peptides) disclosed in application Ser. No. 08/029,333, now U.S. Pat. No. 5,399,667, were used as probes to identify said receptor. These peptides, and more soluble derivatives containing an additional lysine residue, were radiolabeled with $^{125}$I and used in conjunction with a variety of membrane impermeant crosslinking reagents to identify cellular proteins which bind the peptides with high affinity. All of the VVM-containing peptides tested with five different crosslinking reagents specifically labeled a 52 kDa protein, which was also affinity labeled by the recombinant TS1 CBD.

Specifically, after crosslinking peptide to K562 human erythroleukemia cells (ATCC CCL 243) to block the 52 kDa protein, both cell adhesion to and affinity labeling by VVM-containing peptides were inhibited in a concentration dependent manner. Peptide labeling, like cell adhesion, was partially inhibited by heparin and stimulated by EDTA. The 52 kDa protein did not appear to contain glycan chains and was trypsin sensitive. It was recovered in a membrane fraction and was rapidly solubilized with TRITON X-100 and X-114 nonionic detergents. Upon phase separation of TRITON X-114, the 52 kDa protein partitioned into the hydrophobic detergent phase.

The detergent solubilized 52 kDa protein bound selectively to wheat germ agglutinin-SEPHAROSE, and after cell surface labeling with a membrane impermeant biotinylating reagent, bound to streptavidin-SEPHAROSE. Further, fluorescent beads covalently derivatized with the 4N1s [SEQ ID NO: 2] peptide and derivatives thereof specifically decorated intact K562 cells.

In view of the above, it is evident that the properties of the isolated 52 kDa protein are consistent with those of a receptor for the CBD of TS1 and other TS isoforms. That is, the following properties of the 52 kDa protein are consistent with its designation herein as a receptor for the TS1 peptides (4N1s and 7N3 peptide sequences as well as the 4N1K and 4NK peptides, which contain additional lysines for better solubility and crosslinking) and CBD:

The 52 kDa protein has a reasonably high affinity for these peptides.

All VVM-containing peptides and CBD itself label the same protein.

Properties of cell adhesion parallel the properties of labeling of the 52 kDa protein.

The 52 kDa protein is an integral membrane glycoprotein component.

The binding site of the 52 kDa protein is accessible on the intact cell surface.

Prior blockage of the receptor by reaction of cells with the peptides and crosslinking reagent inhibits cell adhesion, as well as affinity labeling.

The 52 kDa protein receptor of the invention thus is useful for in vitro binding (cell attachment) of the 4N1s and 7N3 peptides as described in application Ser. No. 08/029,333, filed Mar. 5, 1993, now U.S. Pat. No. 5,399,667. The CBD region of TS1 from which these peptides are derived also is implicated in the motility of inflammatory cells and tumor cells. Thus, the receptor is further useful in assay procedures for accessing the processes of inflammation, arthritis and cancer metastasis. This receptor has been found on every cell type so far examined by the inventors. It is on endothelial cells of all types and may provide an anchoring point on TS1, thus allowing the enhancement of the angiogenic functions of other identified peptide regions of TS1.

DETAILED DESCRIPTION OF THE INVENTION

While the specification concludes with claims particularly pointing out, and specifically claiming the subject matter regarded as forming the present invention, it is believed that the invention will be better understood from the following preferred embodiments of the invention taken in conjunction with the accompanying drawings in which:

BRIEF DESCRIPTION OF THE DRAWINGS

FIG. 1 shows the amino acid sequences of the peptides described herein. The peptides represent the following amino acids from the TS1 sequence; C4, 1016–1045; C7, 1091–1120; HBDI, 17–35; HBD III, 170–190; MAL I, 368–386; MAL III, 481–499. In peptide 4N1K the N- and C-terminal K residues are non-native as are the N-terminal K and C-terminal KKY residues in peptide 4NK.

FIG. 2A shows the inhibition of labeling of the 52 kDa protein of K562 cells by TS1 peptides. Reaction conditions were as described in Methods described below. Labeled 4N1K was present at 2 µM and the unlabeled peptides each present at 300 µM.

Figure 3:
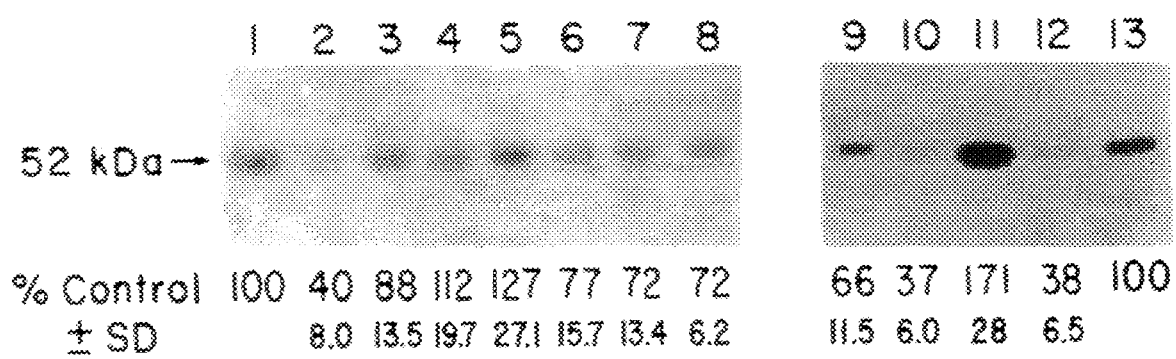

Lanes are: 1 and 8, no additions; 2, 4N1K; 3, 7N3; 4, HBD I; 5, HBD III; 6, Mal I; 7, Mal III.

See FIG. 1 and the Sequence Listing for the sequences of these peptides. Below each band is the percent intensity relative to control lanes 1 and 8, as determined by laser scanning densitometry. Standard deviations (four experiments) are listed below each lane.

FIG. 2B shows the labeling of the 52 KDa protein by recombinant CBD. Recombinant CBD-GST fusion protein (lanes 1–4) or GST alone lanes (5–8) were adsorbed to glutathione-Sepharose. The protein bound to the beads was then reacted with iodinated SASD.

Triton X-100 extract of K562 cells was incubated with the beads which were washed and then photolyzed to crosslink the bound receptor. After reduction the radiolabel was transferred to the crosslinked protein which was detected after SDS-PAGE and autoradiography.

Lane 1, CBD-GST (positive control); lane 2, incubated with Triton X-100 extract in the presence of peptide 4N1K; lane 3, another positive control; lane 4, beads eluted with 4N1K peptide (300 µM) before photolysis. Lanes 5–8 identical conditions to lanes 1–4 except that the beads contained GST alone.

FIG. 3 shows the effect of enzymes, glycosaminoglycans and divalent metals on labeling of the 52 kDa protein of K562 cells with iodinated 4N1K.

Lanes are:

1, control;

2, trypsin 20 µg/ml, 25° C., 90 min.;

3, chymotrypsin 20 µg/ml, 25° C., 90 min.;

4, chondroitinase ABC 1 unit/ml, 37° C. 90 min;

5, chondroitinase AC 1 unit/ml, 37° C. 90 min;

6, chondroitin sulfate A, 100 µg/ml;

7, chondroitin sulfate B,100 µg/ml;

8, chondroitin sulfate C, 100 µg/ml;

9, heparin, 10 µg/ml;

10, heparin, 100 µg/ml;

11, EDTA, 3 mM;

12, Mn++, 4 mM;

13, control for lanes 9 thru 12 (1 mM Ca++ and 1 mM Mg++).

Percent of control labeling determined by laser scanning densitometry is indicated below each lane along with the standard deviation (three experiments).

FIG. 4 shows the labeling of intact cells, lysates and particulate fractions of K562 cells.

Lane 1, labeling of intact cells;

Lanes 2, 3 and 4, the same number of cells were labeled immediately after lysis by freezing/thawing (lane 2), treatment with 1% w/v Triton X-100 (lane 3) and freezing/thawing in 1% w/v Triton X-100 (lane 4).

A cell lysate was prepared by freezing/thawing and centrifuged at 3,000×g for 20 min. The resulting supernatant was then centrifuged for 1 hr at 120,000×g and the supernatant (lane 5) and pellet resuspended to its original volume (lane 6) were labeled. This crude membrane pellet was then treated with Triton X-100 for 1 hr at 4° C. and centrifuged for 1 hr at 120,000×g. The supernatant (lane 7) and resuspended pellet (lane 8) were labeled.

Figure 5A:
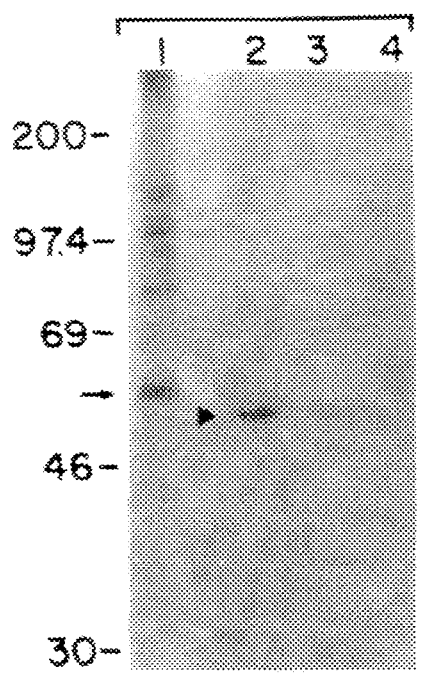
Figure 5B:
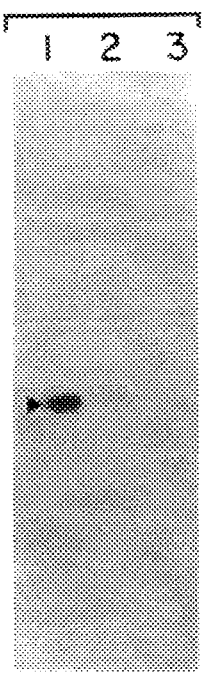
Figure 5C:
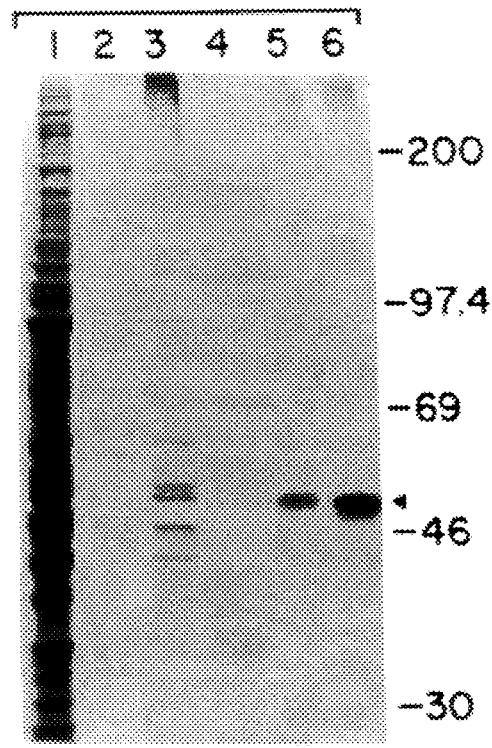

FIGS. 5A, 5B and 5C show, respectively, the glycoprotein nature (A), cell surface localization (B), and hydrophobicity (C) of the affinity labeled protein.

5A. A Triton X-100 solubilized preparation of crude membranes as incubated with wheat germ agglutinin- Sepharose in the absence (lanes 1, 2 and 4) and presence (lane 3) of 0.2 M N-acetylglucosamine. After washing, an aliquot of the beads was labeled with Na$^{125}$I and iodobeads to label all bound proteins (lane 1).

Another aliquot of beads was affinity labeled with iodinated 4N1K and SASD (see Methods; lanes 2, 3 and 4) in the absence (lanes 2 and 3) or presence (lane 4) of unlabeled 4N1K. The arrow in lane 1 indicates the major iodinated protein and the arrowhead in lane 2 indicates the 52 kDa specifically labeled protein. Note that these two do not comigrate.

5B. K562 cells were reacted with the impermeant biotinylation reagent LC-NHS-biotin and washed with free amino acids to react and remove all reagent. Cells were then solubilized with Triton X-100 and the soluble material incubated with streptavidin-Sepharose.

After washing the beads, they were affinity labeled with iodinated 4N1K in the absence (lane 1) or presence (lane 3) of unlabeled 4N1K. Cells which had not been reacted with the biotinylating reagent were treated identically and labeled (lane 2). The arrowhead indicates the 52 kDa protein.

5C. K562 cells were lysed with 1% w/v Triton X-114 at 4° C., and centrifuged to remove debris. The supernatant was then warmed to 40° C. to separate the detergent-rich phase, and centrifuged over a sucrose cushion. The water soluble material in the upper phase and the detergent soluble material in the phase below the sucrose cushion were collected and affinity labeled with 4N1K.

After electrophoresis, the gel was stained with Coomassie blue (lanes 1–3) and autoradiographed (lanes 4–6). Lanes 1 and 4 are the water soluble material which contains the vast majority of the proteins.

Lanes 2 and 5 are the detergent phase diluted to the same original volume as the aqueous phase and lanes 3 and 6 are tenfold more concentrated detergent phase. The arrowhead indicates the 52 kDa protein.

FIGS. 6A, 6B, 6C and 6D show the specific binding of 4N1K derivatized fluorescent beads to the surface of K562 cells. Beads prepared as in Methods hereinbelow were incubated in suspension with the cells at 4° C. for 20 min. in the presence (FIGS. 6A and 6B) or absence (FIGS. 6C and 6D) of 0.5 mM soluble 4N1K peptide.

Figure 6A:
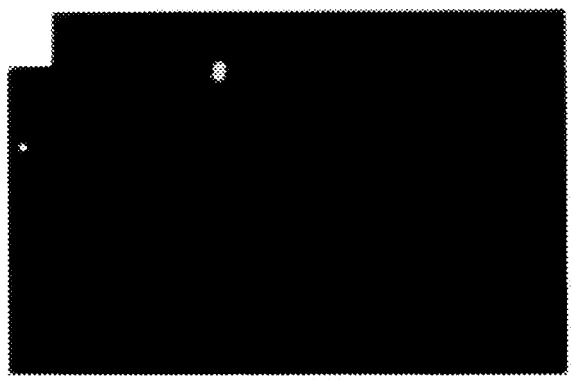
Figure 6B:
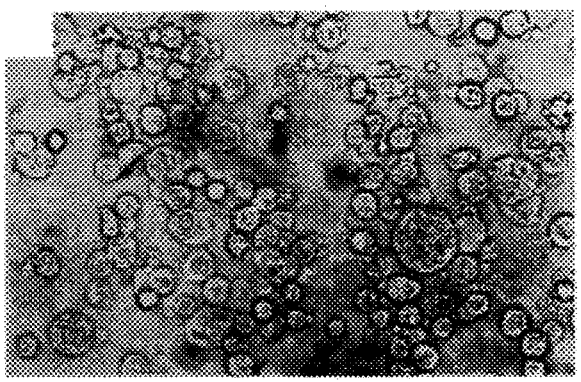
Figure 6C:
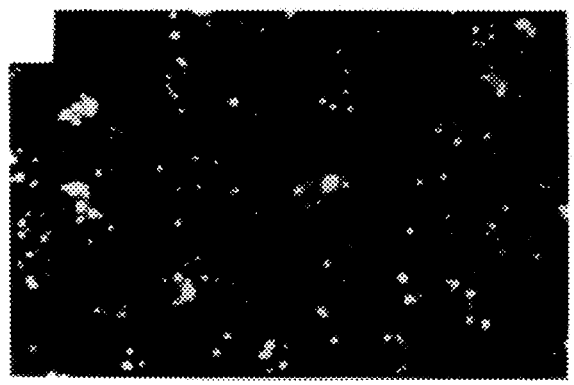
Figure 6D:
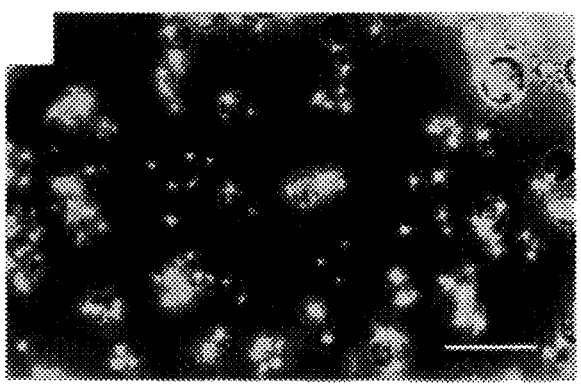

The cells were photographed with epifluorescence illumination alone (FIGS. 6A and 6C) and with simultaneous phase optics and epifluorescence (FIGS. 6B and 6D).

The intensely fluorescent beads are visible even with the phase light source turned on. The bar (FIG. 6D) represents 40 microns.

Figure 7A:
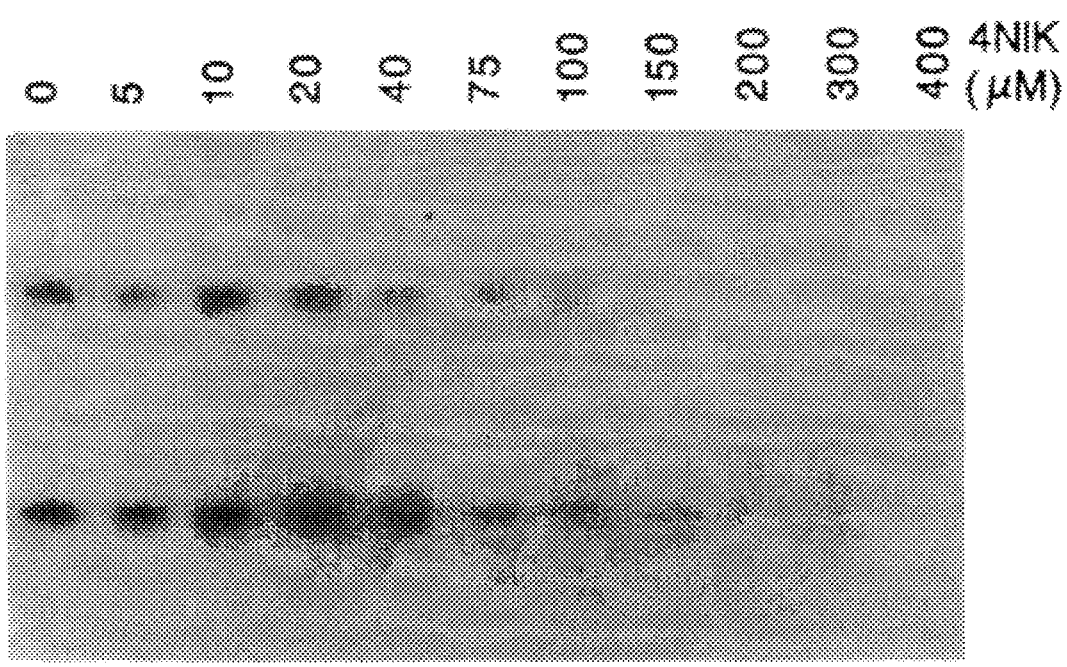
Figure 7B:
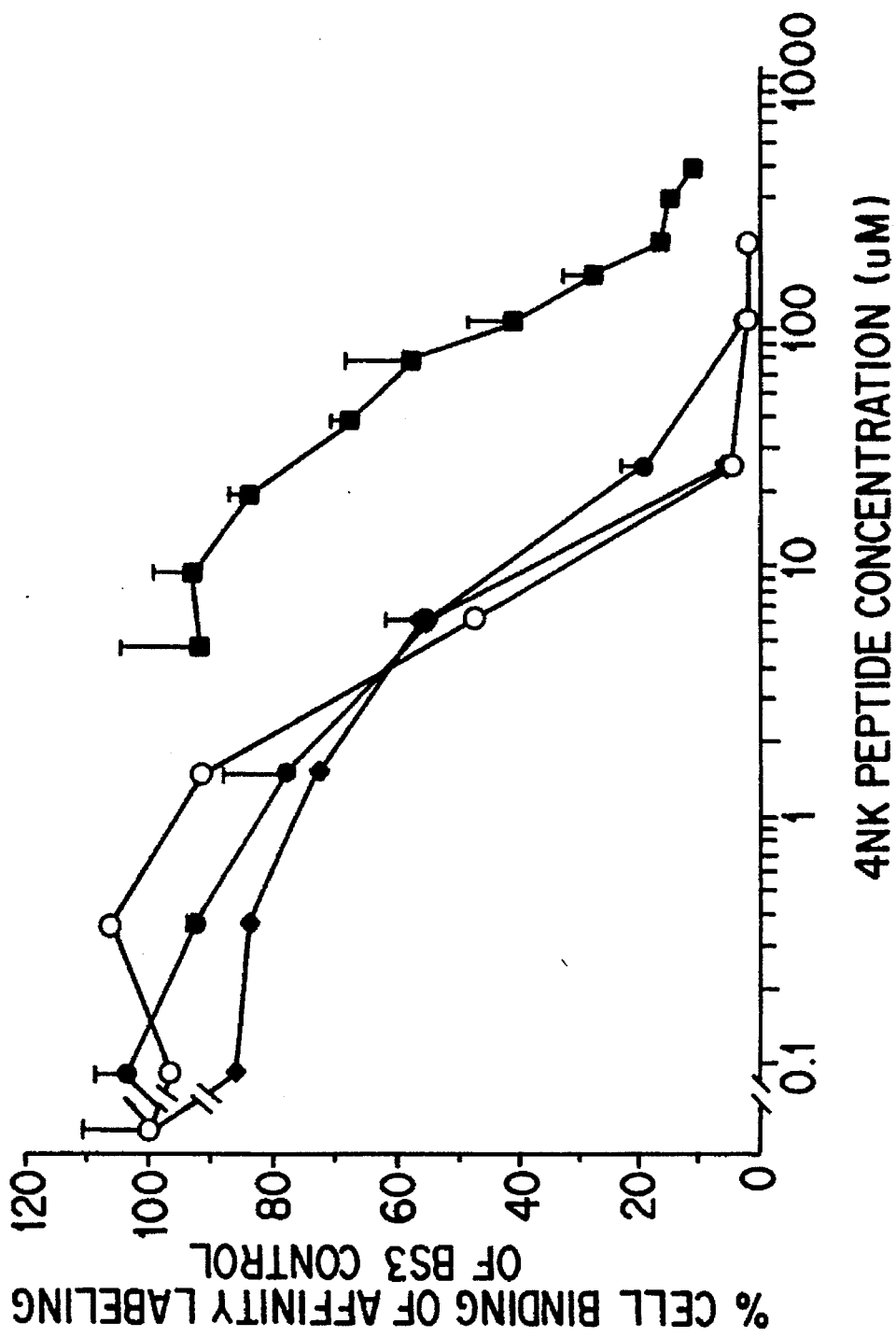

FIGS. 7A and 7B show the blockade of cell adhesion by prior affinity labeling. K562 cells were reacted with peptide 4N1K (FIG. 7A) or 4NK (FIG. 7B) over the concentration range indicated in the presence of 400 μM bis (sulfosuccinimidyl) suberate (BS3).

These cells were then affinity labeled with iodinated SASD and 4N1K. FIG. 7A shows that the prior reaction with 4N1K and BS3 does in fact block the receptor. In this experiment both the 52 and 37 kDa bands were labeled in equal amounts. The labeling was quantified by densitometry and plotted on the graph in FIG. 7B (filled squares). Blocked cells were tested for adhesion to peptides 4NK (open circles), C4 (filled circles) and C7 (filled diamonds). The results are normalized to the positive control (no prior reaction with 4NK, but treated with 400 μM BS3) as 100%.

In order to illustrate the invention in further detail, the following specific laboratory examples were carried out with the results as indicated. Although specific examples are thus illustrated herein, it will be understood that the invention is not limited to these specific examples or the details therein.

EXAMPLES

Materials and Methods

Reagents: All peptides used were synthesized by the Protein Chemistry Facility of Washington University School of Medicine on an Applied Biosystems Model 431 peptide synthesizer as described previously (19). Peptides were evaluated by mass spectrometry before and after purification on HPLC[1]. All crosslinking reagents, Iodobeads, NHS-LC-Biotin, and immobilized streptavidin were from Pierce (Rockford, Ill.). Na$^{125}$I, 100 mCi/ml, carrier free, was obtained from Amersham (Arlington Heights, Ill.). The aldehyde-modified yellow-green fluorescent latex microspheres were the product of Molecular Probes, Inc. (Eugene, Ore.). All other reagents were from Sigma (St. Louis, Mo.).

Cell preparation and lysis: K562 cells were grown and harvested as described (19). 2×10$^6$ cells suspended in buffer B, (buffer A [20 mM HEPES, 150 mM NaCl, pH 7.4] with protease inhibitor cocktail consisting of 40 μg/ml each antipain, pepstatin A, chymostatin, leupeptin, soybean trypsin inhibitor, aprotinin, and 0.5 mM PMSF[1]) were used for affinity labeling of intact cells. Special treatments of cells or reaction conditions are indicated for each experiment (see "Results") or described below. Cells were lysed by freezing/thawing or dissolved in 1% Triton X-100 in buffer B, or 1% Triton X-114 in buffer B for 60 min. at 4° C. followed by centrifugation at 50,000×g for 30 min.

In the experiments to assess the effects of sodium chlorate on affinity labeling the RPMI medium 1640 was modified by replacing MgSO$_4$ with MgCl$_2$ and the concentrations of cystine and methionine were reduced to 10% of their original value. The medium was supplemented with 10% dialyzed fetal calf serum (3 days dialysis against PBS[1]). K562 cells were grown in this modified medium for 3, 5 and 7 days with or without addition of 30 mM sodium chlorate (20).

Treatments of cells with proteases and glycosaminoglycan-degrading enzymes: After washing, 2×10$^6$ cells were resuspended in 200 μl buffer A with or without 1) 20 μg/ml trypsin or chymotrypsin, 2) 1.0 unit/ml chondroitinase ABC or AC, 3) 2.5 units/ml heparinase I, II, or III. The digests were allowed to proceed for 90 min. at 25° C. for proteases and 37° C. for glycosidases (21) respectively. At the end of the incubation, 1 ml of ice-cold buffer B was added to each reaction and the cells were washed with the same buffer.

Crude membrane preparation and Triton X-100 solubilization: Cell suspensions in buffer B were frozen in a dry ice ethanol bath and thawed in a 40° C. water bath three times followed by centrifugation at 3,000×g for 20 min. at 4° C. to remove cell debris and unbroken cells. The supernatant was centrifuged at 120,000×g for 60 min. (4° C.) and the resulting pellet was washed with buffer B. This 120,000×g pellet (crude membranes) (22), was either used for affinity labeling or solubilized in 1% Triton X-100 in buffer B for 60 min. at 4° C. followed by another 60 min. centrifugation at 120,000×g (4° C.). The resulting supernatant was collected as the Triton X-100 extract of crude membranes.

Phase separation in Triton X-114: Cell suspensions or crude membranes were solublized in 1% Triton X-114 in buffer B for 60 min. and centrifuged at 50,000×g for 30 min.

The supernatant was phase separated as described (23). The upper aqueous phase was removed, cooled to ice temperature and received 1% fresh Triton X-114. This solution was again overlaid on the same sucrose cushion used previously, warmed, and then centrifuged above the previous detergent phase. The Triton X-114 extraction and phase separation were repeated a third time. The Triton X-114 phase was then washed once with buffer A to remove any trapped hydrophilic components and the aqueous phase was also re-extracted with 2% Triton X-114 in a separate tube and this last detergent phase was discarded. Finally, Triton X-114 and buffer B were added to the aqueous and detergent phases respectively in order to obtain equal volumes and approximately the same salt and detergent content for both samples.

Wheat germ agglutinin (WGA) binding: Crude membranes or cells were solubilized in 1% Triton X-100 in buffer B as described above. The clear 50,000×g supernatant was incubated for 90 min. at 4° C. with ⅕volume of WGA (leetin from *Triticum vulgaris*) immobilized on cross-linked agarose (23). The beads were recovered by centrifugation and washed with buffer B. The WGA beads were resuspended in buffer A and affinity labeled with $^{125}I$-peptide or $^{125}I$-SASD-peptide followed by washing. All of the proteins adsorbed to the WGA-beads were also iodinated with $Na^{125}I$ using Iodobeads.

Biotinylation of cell surface proteins and binding to immobilized streptavidin: $10^7$ K562 cells suspended in 2 ml buffer B were washed with buffer B and then biotinylated with 4 mg water-soluble NHS-LC-Biotin at 4° C. for 30 min. (24). The labeled cells were washed in buffer B containing 0.1M glycine, and solubilized in 1% (w/v) Triton X-100 as described above. The soluble material was adsorbed. with immobilized streptavidin for 60 min. at 4° C., which was washed extensively and then labeled with $^{125}I$-SASD-4N1K.

Affinity labeling: Affinity labeling of receptor candidate proteins by iodinated peptides was performed in 1.5 ml microfuge tubes in a final volume of 200 μl. Reactions were stopped by washing with buffer A and centrifugation or heating in a boiling water bath immediately after addition of SDS sample buffer. G361 and CPAE cells were grown in 24 well culture plates and labeled after washing with buffer B while still attached to the wells. For the experiments using $BS^3$ [Bis(sulfosuccinimidyl) suberate] (25) or other homobifunctional cross linking reagents such as Sulfo-DST (Disulfosuccinimidyl tartarate) and Sulfo-EGS [Ethylene glycolbis(sulfo-succinimidylsuccinate)], peptides were iodinated by incubation with $Na^{125}I$ and pre-washed Iedo-Beads for 5 min. in buffer A at room temperature to give a specific radioactivity between 50 and 100 Ci/mmol. The radiolabeled peptides were incubated with cells or other receptor-containing samples at a final concentration of 2 μM (or varying concentrations) for 20 min. on ice. Then the $BS^3$ was added to the specified concentration (routinely 10 μM) and incubated another 30 min. on ice.

SASD [Sulfosuccinimidyl 2-(p-azidosalicylamido)ethyl-1-3'-dithiopropionate] (26) and APDP {N-[4-(p-azidosalicylamido)butyl]-3'-(2'-pyridyldithio) propionamide} were also used as cross linkers. Both of these heterobifuctional reagents are iodinatable, cleavable, and photoreactive crosslinkers but are chemically reactive with different groups on the peptides. Briefly, SASD or APDP was first radio-labeled by $Na^{125}I$ with Iodobeads in the dark. Radiolabeled SASD or APDP (used with cysteine containing peptides) was conjugated to the peptides at molar ratios of crosslinker: peptide of 1:1 to 3:1 for 2 hr. in the dark at room temperature. These conjugated complexes with a peptide concentration of 20 μM were either used directly or passed through a 5 ml 100–200-mesh P-2 column (Bio-Rad) as described (27). After a 20 min. incubation of these radiolabeled, activated peptides with samples (in the dark, on ice) irradiation with long wave (360 nm) UV light was carried out for 15 min. on ice.

After peptide affinity labeling all samples were dissolved in SDS sample buffer (with or without reducing agent), boiled for 10 min. and separated on a 7.5% SDS-PAGE[1] gel (28). The gels were soaked in 5% glycerol for 5 min. or stained and dried. Autoradiography was performed for I to 24 hr. at −70° C. with intensifying screens. Exposed films were quantified by scanning with an LKB 2222-010 Ultroscan XL laser densitometer.

Expression of CBD-GST[1] fusion protein and affinity labeling. The Cla I to Bel I fragment of TS1 cDNA (17) was cloned into the pGEX-2T vector (Pharmacia) in frame with the glutathione-S transferase (GST[1])coding region. After growth, induction with IPTG and cell lysis, the supernatants were adsorbed onto glutathione-Sepharose beads. The extensively washed CBD-GST or GST (control) beads were radiolabeled with 2 μM $^{125}I$-SASD-4N1K. These bead complexes were incubated with K562 cell lysates in Triton X-100, photolyzed (360 nM UV), and extensively washed.

Preparation and binding to cells of fluorescent 4N1K-Beads: Covalent coupling of 4N1K peptide to aldehyde-modified latex beads followed the product instructions with slight modification. One ml of a 2% aqueous suspension of aldehyde latex beads was added to 2 mg of 4N1K peptide solution in 1 ml of 50 mM phosphate buffer, pH 6.5. 10 mg of sodium cyanoborohydride was added to this mixture followed by incubation at 25° C. overnight for complete coupling and reduction. The control beads were reacted with 10 mg of glycine instead of 4N1K peptide and were treated as above. The reaction was stopped and the unreacted sites on the fluorescent latex beads were blocked by addition of 10 ml of 1% BSA[1] in 50 mM phosphate buffer, pH 7.4 containing 0.9% NaCl (PBS). Then unreacted peptide (or glycine) was separated from the peptide-coupled latex beads by washing. The washed beads were resuspended in 2 ml of the same buffer and gently sonicated in a bath sonicator. The conjugated fluorescent beads were diluted 1,000 fold with 1% BSA in PBS and sonicated as above. About $10^7$ K562 cells (in 0.5 ml of 1% BSA in PBS) were mixed with 0.5 ml of latex beads and incubated at 4° C. with gentle rocking for 20 min. To inhibit specific binding of the beads, some reactions contained 0.5 mM soluble 4N1K peptide. The cells were extensively washed and resuspended in 0.5 ml of the same buffer. 40 μl of this cell suspension was pipetted onto poly-L-lysine-coated slides and observed immediately (400×fluorescein epi-illumination) (29).

Cell adhesion assays were performed as described (18, 19).

RESULTS

IT IS DISCLOSED in application Ser. No. 08/029,333, now U.S. Pat. No. 5,399,667, that two peptides, 4N1s and 7N3, from the C-terminal CBD of TS1 are responsible for the cell attachment activity of this region of TS1 (18,19, FIG. 1). For crosslinking experiments, these shorter peptides were initially selected since they are nearly as active in cell attachment assays as their longer and less soluble parent sequences (19).

To further increase solubility and add additional amino groups for reaction with crosslinking reagents, peptides 4N1s and 4N1 were modified by the addition of lysine residues at both the amino- and carboxyl-termini to give peptides 4N1K and 4NK respectively (FIG. 1).

Peptide 4NK also contains an additional tyrosine residue to provide another iodination site. Several homobifunctional hydroxysuccinimide esters of varying spacer chain length were tested (including Sulfo-DST, $BS^3$ and Sulfo-EGS) over a wide concentration range.

In addition, heterobifunctional reagents such as APDP and SASD which contain an iodinatable, photolabile group were tested. All of these reagents are water soluble sulfonated compounds that are membrane impermeant (25) and hence should label cell surface proteins preferentially. All reagents and labeling conditions were first tested using K562 human erythroleukemia cells (ATCC CCL 241), which are nonadherent during growth but attach well to TS1 and CBD peptides coated on plastic (18,19).

In addition, human melanoma, G361, (ATCC CRL 1424), and calf pulmonary artery endothelial (CPAE) cells were labeled while still attached to plastic wells in which they were grown. All three cell types gave identical results. The crosslinker reagent concentration dependence (0 to 3 mM) of affinity labeling by $^{125}$I-4N1K (at 10 µM) was examined for $BS^3$ S-DST and S-EGS All of these reagents caused radiolabeling of a prominent band at an Mr of 52 kDa and, in some experiments, a band at 37 kDa. At the highest concentrations of crosslinker, a large covalent aggregate began to form which did not enter the separating gel.

The heterobifunctional reagents SASD and APDP, when used with 4N1K, also yielded the same labeled bands at 52 and 37 kDa. The apparent mobilities of these bands were similar with or without reduction of the SDS gel samples prior to eletrophoresis, even when the cleavable reagent SASD, which transfers the iodinated group to the reactive protein was used.

Affinity labeling with iodinated peptide 7N3 also revealed a major band at 52 kDa and a minor band at 37 kDa. For all conditions of labeling, the intensity of the lower 37 kDa band was quite variable from one experiment to another, being entirely absent in some cases. However, the 52 kDa band was always observed.

For further characterization of these labeled proteins, iodinated 4N1K was used with the reagent $BS^3$ or SASD. All experiments were performed on both K562 cells in suspension and CPAE cells attached to plastic. Most experiments were also performed on G361 cells. All three cell types gave the same labeling patterns with these reagents, with the exception that the CPAE cells labeled while attached to plastic revealed an additional labeled band at Mr ca. 250 kDa, which appeared to be associated with the extracellular matrix. This protein was not extractable into Triton X-100 and the intensity of its labeling increased as the cells become confluent and elaborated increased amounts of matrix.

At sufficient excess of unlabeled 4N1K peptide, labeling of the 52 kDa protein by iodinated 4N1K could be almost completely blocked. To further explore the specificity of labeling by 4N1K, reactions were performed in the presence of other unlabeled peptides from different regions of TS1 (FIG. 2).

First, as expected from the fact that both 4N1s and 7N3 mutually inhibit cell adhesion to either peptide, both 4N1K (lane 2) and 7N3 (lane 3) inhibited affinity labeling of the 52 kDa band by iodinated 4N1K. The experiment in FIG. 2 shows a case in which labeling of the 37 kDa protein was completely absent. Specificity was also indicated by the lack of substantial inhibition of labeling by peptides from other TS1 domains.

For example, two peptides from the N-terminal heparin-binding domain of TS1 (lanes 4 and 5) showed little inhibition of labeling as did peptides from the type 1 or malaria-like repeats of TS1 (lanes 6 and 7). Unlabeled peptides in lanes 4, 5 and 7 bind cells, but through receptors distinct from the one identified here.

In the obverse of this experiment, six other peptides from different domains of TS1 were iodinated and used with all five crosslinking reagents to determine if the same or additional bands could be labeled. In no other case was the 52 (or 37) kDa band labeled.

Peptides removed from the context of their native protein structures may display binding activities that are not representative of the proteins themselves. Thus the entire CBD was used as an affinity label to determine if it identified the same protein as the CBD peptides. To do this, CBD was expressed in E. coli as a fusion protein with GST and then adsorbed on glutathione-Sepharose beads. GST alone was used as the control.

The beads were reacted with iodinated SASD which coupled to the amino groups on the CBD and GST. The beads were then incubated with Triton X-100 extracts of K562 cells in the absence and presence of 4N1K peptide to allow binding of the solubized receptor candidates to the beads. One sample was also eluted with 4N1K peptide after binding of receptor to the beads. The beads were then photolyzed to crosslink the bound proteins.

Upon reduction in SDS sample buffer, the iodine-labeled moiety was transferred to the receptor protein with concomitant cleavage of the crosslink.

FIG. 2B shows the results of such an experiment. Lane 1 shows the CBD-GST mediated labeling of a 52 kDa protein. No other protein bands were labeled. In lane 2, soluble 4N1K peptide was included during the binding of the Triton X-100 extract to the CBD-GST beads. Lane 3 is another CBD-GST positive control and in lane 4, the CBD-GST beads were eluted with 4N1K peptide before photolysis. Lanes 5 through 8 show samples treated identically to lanes 1 through 4, except that the matrix contained immobilized GST alone. No protein bands were visualized. Thus a protein of the same molecular weight is affinity labeled by the CBD as by the peptides derived from it.

To begin determining the properties of this 52 kDa receptor, the sensitivity of the labeled bands to various treatments of the cells was examined. In FIG. 3, lane 1 is control labeling (no treatments), while lanes 2 and 3 show the results of treatment of the cells (prior to labeling) with trypsin and chymotrypsin. Trypsin treatment resulted in a substantial reduction in labeling of the 52 kDa band while chymotrypsin had little effect. Lanes 4 and 5 show results of prior treatment of the cells with chondroitinase ABC and AC respectively. Neither reduced the intensity of labeling or shifted the position of the labeled band.

To determine the effects of glycosaminoglycans on labeling, chondroitin sulfates A, B and C (lanes 6, 7 and 8) were included at 100 µg/ml during the incubation with labeled 4N1K. All three had little effect on the intensity of labeling. Heparin at 10 µg/ml reduced labeling to about the same extent as the chondroitin sulfates at 100 µg/ml, while heparin at 100 µg/ml showed a more substantial inhibition of labeling (lanes 9 and 10). These data are consistent with the effects of glycosaminoglycans on the adhesion of cells to peptides 4N1s and 7N3 (18,19).

To determine if the 4N1K peptide was interacting directly with a heparin (heparan) sulfate chain of the 52 kDa protein, cells were treated with heparinase I, II and III singly and in combination before labeling with iodinated 4N1K. None of the enzymes had any effect on either the intensity of labeling of the 52 kDa protein or its mobility on SDS gels.

To further determine if sulfated glycosaminoglycans participate in binding of peptide to the 52 kDa protein, K562 cells were grown in medium in which sulfate was replaced by chlorate. This allows depletion of endogenous sulfated macromolecules and prevents new synthesis of sulfated carbohydrates (20,30). Cells were labeled with iodinated 4N1K after 3, 5 and 7 days in chlorate-containing medium. The intensity and size of the labeled protein were identical to that seen in control cells grown in parallel in normal sulfate-containing medium. Thus the 52 kDa protein does not appear to contain sulfated carbohydrate chains as part of its structure. The inhibitory effects of high concentrations of heparin are probably due to the heparin-binding activity of the 4N1K peptide.

Initial labeling experiments were performed in a buffer containing 1 mM each calcium and magnesium. To determine if divalent metals were required for labeling the 52 kDa protein, K562 cells were labeled in buffer A containing 3 mM EDTA (FIG. 3, lane 11). Cells were also labeled in the presence of 4 mM manganese (lane 12). The control in 1 mM calcium and magnesium is in lane 13. EDTA appeared to enhance labeling somewhat while Mn++ reduced labeling.

To assess the cellular localization of the putative TS receptor, the labeling of intact cells was compared with that seen when cells were lysed. As seen in FIG. 4, the intensity of labeling of the 52 kDa and 37 kDa bands was actually greater when intact cells were labeled (lane 1) than when cells were first lysed by freezing/thawing (lane 2), by 1% Triton X-100 (lane 3) or by a combination of freezing/thawing in the presence of detergent (lane 4). The lysates were prepared in a protease inhibitor cocktail (see Methods) and labeled immediately.

These results suggest that a large fraction of the protein is available on the surface of intact cells. Indeed, the immediate decrease in labeling intensity upon cell lysis by two methods suggests that the affinity of the receptor protein may be dependent in some way on an intact plasma membrane.

Cells were lysed by freezing/thawing and debris removed by low speed centrifugation. The supernatant was then separated into a soluble (lane 5) and insoluble (lane 6) fraction by centrifugation at 120,000×g, and both fractions labeled. 88% (+/−1.7) of the labeled 52 kDa band was recovered in the particulate fraction. This crude membrane fraction was extracted with 1% Triton X-100 and centrifuged at 120,000×g. After detergent treatment, the majority (75.3% +/−3.6) of the labelable 52 kDa protein was found in the soluble fraction (lane 7) instead of the insoluble pellet (lane 8).

Many extracellularly oriented membrane proteins contain oligosaccharides that bind to the lectin wheat germ agglutinin (WGA). In addition, cell adhesion to the TS1 C-terminal peptides is inhibited selectively by WGA and not by other lectins such as Lens culinaris agglutinin and concanavalin A. To determine if the 52 kDa receptor candidate is a WGA binding glycoprotein, Triton X-100 solubilized material was adsorbed to WGA-Sepharose in the presence and absence of the hapten sugar inhibitor Nacetylglucosamine (at 0.2M). The beads were washed extensively and then labeled with $Na^{125}I$ and iodobeads to label all bound proteins. Aliquots of the same beads were also labeled with $^{125}I$-SASD-4N1K to label the 52 kDa protein.

As seen in FIG. 5A, lane 1, many proteins bound to the WGA matrix. Lanes 2 and 3 show that the 52 kDa protein labeled by iodinated 4N1K does indeed bind to WGA-Sepharose and that the hapten sugar N-acetylglucosamine blocks most of this binding. The major labeled protein (lane 2) has an Mr of 52 kDa and comigrated with the band labeled on intact cells. Lane 4 shows that the 4N1K labeling of the protein bound to WGA-Sepharose was blocked by unlabeled 4N1K. It is noteworthy that the labeled 52 kDa band did not comigrate with any of the major proteins iodinated with $Na^{125}I$ in lane 1, further attesting to the affinity and specificity of the labeling.

These data suggest an external orientation for the 52 kDa protein. To confirm this, intact cells were reacted with NHS ester-biotin (long chain), a non-cleavable cell surface biotinylation reagent.

The labeled cells were washed in a buffer contain 0.1M-free amino acids to react and remove any remaining biotinylation reagent and then solubilized in 1% Triton X-100. The soluble material was adsorbed with streptavidin-Sepharose, which was washed extensively, and then labeled with iodinated 4N1K. As seen in FIG. 5B, lane 1, the only labeled band was at 52 kDa, and the labeling was blocked by unlabeled 4N1K (lane 3). Cell extracts treated in the same manner but without prior biotinylation of the intact cells revealed no labeled 52 kDa protein (lane 2).

The intense labeling of intact cells by 4N1K, the binding of the 52 kDa protein to WGA-Sepharose and its biotinylation on intact cells all indicate that this putative TS receptor is located primarily at the cell surface. Such a receptor would likely be a transmembrane protein, and contain a hydrophobic region as part of its structure.

To test this proposal, the detergent Triton X-114 was employed (32,33). At low temperatures (i.e. at 4° C.) this detergent acts like Triton X-100, and in fact solubilizes the 52 kDa band in active form as judged by labeling with iodinated 4N1K. When the temperature is raised to 40° C., however, Triton X-114 separates from the aqueous phase and forms a dense, hydrophobic detergent phase into which many integral membrane proteins partition (22, 32, 33). Thus recovery in the detergent phase is diagnostic for hydrophobic character. K562 cells were lysed in Triton X-114 and the soluble detergent extract separated at high temperature resulting in an upper aqueous phase and a detergent phase.

Both phases were adjusted to the initial volume and detergent concentration of the original lysate and affinity labeled with 4N1K. As shown in FIG. 5C, the vast majority of the cellular protein remained in the aqueous phase after raising the temperature (protein stain, lane 1) while no 4N1K labeled 52 kDa band could be detected in this phase (lane 4).

When an equivalent volume of the resuspended detergent phase was run on the gel no protein-stained bands were even visible (lane 2). However, the labeled 52 kDa band was readily detected (lane 5). A few protein bands were seen in lane 3 when 10 times more sample was applied and the labeled band (lane 6) was proportionally heavier. The 4N1K labeled 52 kDa protein did not comigrate with any of the major bands visualized with protein staining of the Triton X-114 pellet material in lane 3.

Interestingly, the 37 kDa protein labeled with 4N1K appeared in the aqueous phase in these experiments (faint band in lane 4) suggesting that it is not hydrophobic.

Taken together with the observation that it appears in variable amounts, primarily after cell lysis, and that its labeling properties are identical to those of the 52 kDa protein, the aqueous solubility of the 37 kDa protein suggests that it may be a cleaved, extracellular domain of the intact, hydrophobic 52 kDa receptor protein.

To confirm the cell surface orientation of the 4N1K binding protein, fluorescent beads were covalently derivatized with 4N1K peptide. The beads were incubated with K562 cells in suspension in the presence and absence of solution phase 4N1K peptide, washed and photographed with epifluorescence illumination. As seen in FIG. 6A and B, cells bound virtually no beads in the presence of soluble 4N1K peptide. However, the K562 cells avidly bound the 4N1K derivatized beads (FIGS. 6C and 6D) in the absence of competing peptide. In addition, cells bound few beads derivatized with glycine instead of 4N1K.

To address the relationship of the affinity labeled cell surface 52 kDa protein to the receptor by which cells attach to the CBD of TS1 and the peptides derived from it, K562 cells were reacted with a concentration range (0 to 400 µM) of unlabeled 4N1K peptide in the presence of 400 µM BS$^3$. These cells should thus have a blocked receptor. This was tested in two ways.

First, the blocked cells were affinity labeled with peptide 4N1K using the photolabile reagent SASD (see Methods, hereinbefore). As seen in FIG. 7A, this subsequent labeling was inhibited by the prior reaction with BS$^3$ and 4N1K. The concentration of 4N1K resulting in half maximal inhibition of the subsequent affinity labeling was 80 µM. Secondly, BS$^3$ and 4NK reacted cells were tested for adhesion to plastic wells coated with peptide 4NK and the longer version of the active CBD peptides C4 and C7 (see FIG. 1 for sequences). This adhesion was also inhibited in a dose dependent manner, but here half maximal inhibition was observed with the cells reacted with 8 µM 4 NK peptide (FIG. 7B).

With this same protocol, reaction of the cells with BS$^3$ and intact TS1 at 300 µg/ml, instead of peptide 4NK, resulted in a 50% inhibition of both subsequent affinity labeling with SASD and cell adhesion to the CBD peptides. Thus this experiment directly demonstrates that the 52 kDa protein which reacts with BS$^3$ and 4N peptides is responsible for the binding of cells to the peptides in a cell adhesion assay. Given the qualitative physical differences between the cell adhesion assay and the affinity labeling with SASD, it is remarkable that the concentration dependence of inhibition of these two assays differs by only ten fold.

Various other examples will be apparent to the person skilled in the art after reading the present disclosure without departing from the spirit and scope of the invention. It is intended that all such other examples be included within the scope of the appended claims.

ABBREVIATIONS

The abbreviations used are: TS, thrombospondin; TS-1, thrombospondin-1; CBD, cell binding domain; HBD, heparin binding domain; CPAE, calf pulmonary artery endothelial; WGA, wheat germ agglutinin; BS$^3$, Bis (sulfosuccinimidyl) suberate; Sulfo-DST, Disulfosuccinimidyl tartarate; Sulfo-EGS, Ethylene glycolbis(sulfosuccinimidylsuccinate); SASD Sulfosuccinimidyl 2-(p-azidosalicylamido)ethyl-1-3'-dithiopropionate; APDP, N-[4-(p-azidosalicylamido)butyl]-3'-(2'-pyridyldithio)propionamide: HPLC, high performance liquid chromatography; BSA, bovine serum albumin; PBS, phosphate buffer saline; PMSF, phenylmethylsulfonyl fluoride; SDS-PAGE, SDS-poly acrylamide gel electrophoresis; NHS, N-hydroxysuccinimide; GST, glutathione-S-transferase.

REFERENCES

1. Adams, J., and Lawler, J., (1993) Curr. Biol. 3, 188–190
2. Iruela-Arispe, M. L., Liska, D. J., Sage, E. H., and Bornstein, P. (1993) Devel. Dyna. 197, 40–56
3. Raugi, G. J., Oleud, J. E., and Gown, A. M. (1987) J. Inves. Derm. 89, 551–554
4. Reed, M. J., Puolakkainen, P., Lane, T. F., Dickerson, D., Bornstein, P., and Sage, E. H. (1993) J. Histochem. Cytochem. 41, 1467–1477
5. Castle, V., Varani, J., Fligiel, S., Prochownik, E. V., and Dixit, V. (1991) J. Clin. Inves. 87, 1883–1888
6. Good, D. J., Polverini, P. J., Rastinejad, F., Le Beau, M. M., Lemons, R. S., Frazier, W. A., and Bouck, N., (1990) Proc. Natl. Acad. Sci. U.S.A. 87, 6624–6628
7. Tolsma, S. S., Volpert, O. V., Good, D. J., Frazier, W. A., Polverini, P. J., and Bouck, N. (1993) J. Cell Biol. 122, 497–511
8. Iruela-Arispe, M. L., Bornstein, P., and Sage, H. (1991) Proc. Natl. Acad. Sci. U.S.A. 88, 5026–5030
9. Sun, X., Mosher, D. F. and Rapraeger, A. (1989) J. Biol. Chem. 264, 2885–2889
10. Murphy-Ullfich, J. E., Westrick, L. G., Esko, J. D., and Mosher, D. F. (1988) J. Biol. Chem. 263, 6400–6406
11. Roberts, D. D., Hayerstick, D. M., Dixit, V. M., Frazier, .W. A., Santoro, S. A., and Ginsburg, V. (1985) J. Biol. Chem. 260, 9405–9411
12. Lawler, J., and Hynes, R. O. (1989) Blood, 74, 2022–2027
13. Prater, C. A., Plotkin J., Jaye, D., and Frazier, W. A. (1991) J. Cell Biol. 112, 1031–1040
14. Li, W-X., Howard, R. J., and Leung, L. L. K. (1993) J. Biol. Chem. 268, 16179–16184
15. Asch, A. S., Liu, L, Briccetti, F. M., Barnwell, J. W., Kwakye-Berko, F., Dokun, A., Goldberger, J., Pernambuco, M. (1993) Science, 262, 1436–1440
16. Frazier, W. A., Prater, C. A., Jaye, D., and Kosfeld, M. D. (1993) Thrombospondin, Lahav, J. ed., CRC Press, Boca Raton, PP. 91–109
17. Kosfeld, M. D., Pavlopoulos, T. V., and Frazier W. A. (1991) J. Biol. Chem. 266, 24257–24259
18. Kosfeld, M. D., and Frazier W. A. (1992) J. Biol. Chem. 267, 16230–16236
19. Kosfeld, M. D., and Frazier W. A. (1993) J. Biol. Chem. 268, 8808–8814
20. Rapraeger, A. C., Krufka, A., Olwin B. B. (1991) Science, 252, 1705–1708
21. Sundblad, G., Holojda, S., Roux, L., Varki, A., and Freeze, H. H. (1988) J. Biol. Chem. 263, 8890–8896
22. McGregor, J. L., Catimel, B., Parmenitier, S., Clezardin, P., Dechavanne, M., and Lueng L. L. K. (1989) J. Biol. Chem. 264, 501–506
23. Tandon, N. N., Lipsky, R. H., Burgess, W. H., and Jamieson G. A. (1989) J. Biol. Chem. 264, 7570–7575
24. Ingalls, H. M., Goodloe-Holland, C. M., and Luna, E. J. (1986) Proc. Natl. Acad. Sci. USA, 83, 4779–4783
25. Staros, J. V. (1982) Biochemistry, 21, 3950–3955
26. Shephard, E. G., Beer, F. C. D., Holt, C. V., and Hapgood, J. P. (1988) Anal. Biochem. 168, 306–313
27. Sorensen, P., Farbet, N. M., and Krystal, G. (1986) J. Biol. Chem. 261, 9094–9097
28. Laemmli, U. K. (1970) Nature. 227, 680–685
29. Janssen, K. (1993) Current Protocols in Molecular Biology, Vol. 2, PP 14.6.2–14.6.3
30. Imai, Y., Lasky, L. A., & Rosen, S. D. (1993) Nature, 361, 555–557
31. Kirchhofer, D., Gailit, J., Ruoslahti, E., Grzesiak, J., and Pierschbacher, M. D. (1990) J. Biol. Chem. 265, 18525–18530
32. Bordier, C. (1981) J. Biol. Chem. 256, 1604–1607
33. Greenwalt, D. E., Watt, K. W. K., So, O. Y., and Jiwani, N. (1990) Biochem. 29, 7054–7059
34. Newman, P. J., Knipp, M. A., and Kahn, R. A. (1982) Thromb. Res. 27, 221–224

35. Yabkowitz. R. and Dixit, V. M. (1991) *Cancer Res.* 51, 3648–3656

36. Tuszynski, G. P., Rothman, V. L., Papale, M., Hamilton, B. K., and Eyal, J. (1993) *J. Cell Biol.* 120, 513–521

---

What is claimed:

1. An isolated 52 kDa protein receptor of the COOH-terminal cell-binding domain peptides adjacent to the RGD sequence in the last of the type 3 repeats in the linear amino acid sequence of thrombospondin 1 having the following characteristics:

(a) VVM-containing peptides label said protein receptor, (b) the property of endothelial cell adhesion to said VVM containing peptides, wherein said endothelial cell contains said protein receptor, parallels the property of radio-labeling of said protein receptor by said VVM-containing peptides, (c) said protein receptor is an integral membrane glycoprotein component, (d) the VVM containing peptide binding site of said protein receptor is accessible to binding on the intact cell surface of said endothelial cell, (e) prior blockage of said protein receptor by reaction of said endothelial cell containing said protein receptor with said cell-binding domain peptides and cross linking reagent inhibits said endolethial cell adhesion, and (f) said protein receptor mediates said adhesion of said endothelial cell to said cell-binding domain of thrombospondin 1.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Arg  Phe  Tyr  Val  Val  Met  Trp  Lys  Gln  Val  Thr  Gln  Ser
1                  5                            10
```

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Arg  Phe  Tyr  Val  Val  Met  Trp  Lys
1                  5
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Arg  Phe  Tyr  Val  Val  Met
1                  5
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Phe  Ile  Arg  Val  Val  Met  Tyr  Glu  Gly  Lys  Lys
1                  5                            10
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Ile Arg Val Val Met
1               5

( 2 ) INFORMATION FOR SEQ ID NO:6:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Lys Arg Phe Tyr Val Val Met Trp Lys Gln Val Thr Gln Ser Lys Lys
1               5                   10                  15
Tyr ( 2 ) INFORMATION FOR SEQ ID NO:7:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Lys Arg Phe Tyr Val Val Met Trp Lys Lys
1               5                   10

( 2 ) INFORMATION FOR SEQ ID NO:8:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Arg Phe Tyr Val Val Met Trp Lys Gln Val Thr Gln Ser Tyr Trp Asp
1               5                   10                  15
Thr Asn Pro Thr Arg Ala Gln Gly Tyr Ser Gly Leu Ser Val
                20                  25                  30

( 2 ) INFORMATION FOR SEQ ID NO:9:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Arg Trp Arg Leu Ser His Arg Pro Lys Thr Gly Phe Ile Arg Val Val
1               5                   10                  15
Met Tyr Glu Gly Lys Lys Ile Met Ala Asp Ser Gly Pro Ile
                20                  25                  30

( 2 ) INFORMATION FOR SEQ ID NO:10:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Glu Leu Thr Gly Ala Ala Arg Lys Gly Ser Gly Arg Arg Leu Val Lys
1               5                   10                  15

Gly Pro Asp ( 2 ) INFORMATION FOR SEQ ID NO:11:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( x i ) SEQUENCE DESCRIPTION: SEQ ID NO:11:

Thr Arg Asp Leu Ala Ser Ile Ala Arg Leu Arg Ile Ala Lys Gly Val
1               5                   10                  15

Asn Asp Asn Phe
          20

( 2 ) INFORMATION FOR SEQ ID NO:12:

( i ) SEQUENCE CHARACTERISTICS:
( A ) LENGTH: 19 amino acids
( B ) TYPE: amino acid
( D ) TOPOLOGY: linear ( i i ) MOLECULE TYPE: peptide ( x i ) SEQUENCE DESCRIPTION: SEQ ID NO:12:

Ser Glu Trp Thr Ser Ala Ser Thr Ser Ala Gly Asn Gly Ile Gln Gln
1               5                   10                  15

Arg Gly Arg ( 2 ) INFORMATION FOR SEQ ID NO:13:

( i ) SEQUENCE CHARACTERISTICS:
( A ) LENGTH: 19 amino acids
( B ) TYPE: amino acid
( D ) TOPOLOGY: linear ( i i ) MOLECULE TYPE: peptide ( x i ) SEQUENCE DESCRIPTION: SEQ ID NO:13:

Ser Pro Trp Asp Ile Ala Ser Val Thr Ala Gly Gly Gly Val Gln Lys
1               5                   10                  15

Arg Ser Arg